United States Patent
Bhunia et al.

(10) Patent No.: US 7,787,947 B2
(45) Date of Patent: Aug. 31, 2010

(54) METHOD AND APPARATUS FOR USING AN OPTICAL HEMODYNAMIC SENSOR TO IDENTIFY AN UNSTABLE ARRHYTHMIA

(75) Inventors: Sourav Bhunia, Shoreview, MN (US); Walter H. Olson, North Oaks, MN (US); Can Cinbis, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 1157 days.

(21) Appl. No.: 11/394,477

(22) Filed: Mar. 31, 2006

(65) Prior Publication Data

US 2007/0239215 A1  Oct. 11, 2007

(51) Int. Cl.
*A61N 1/00* (2006.01)

(52) U.S. Cl. .......................................................... 607/6

(58) Field of Classification Search ..................... 607/4, 607/5, 6, 17, 22; 600/322, 323, 339, 443; 708/200

See application file for complete search history.

(56) References Cited

U.S. PATENT DOCUMENTS

| | | | |
|---|---|---|---|
| 4,202,339 A | 5/1980 | Wirtzfeld et al. | |
| 4,750,495 A | 6/1988 | Moore et al. | |
| 4,870,968 A | 10/1989 | Wiertzfeld et al. | |
| 5,176,137 A | 1/1993 | Erickson et al. | |
| 5,213,098 A | 5/1993 | Bennett et al. | |
| 5,431,172 A | 7/1995 | Hoegnelid et al. | |
| 5,601,611 A | 2/1997 | Fayram et al. | |
| 6,144,444 A | 11/2000 | Haworth et al. | |
| 6,144,866 A | 11/2000 | Miesel et al. | |
| 6,198,952 B1 | 3/2001 | Miesel | |
| 6,491,639 B1 | 12/2002 | Turcott | |
| 6,675,031 B1 | 1/2004 | Porges et al. | |
| 6,697,655 B2 | 2/2004 | Sueppel et al. | |
| 6,795,732 B2 | 9/2004 | Stadler et al. | |
| 6,801,797 B2 | 10/2004 | Mannheimer et al. | |
| 6,832,113 B2 | 12/2004 | Belalcazar | |
| 6,836,679 B2 | 12/2004 | Baker, Jr. et al. | |
| 6,873,870 B2 | 3/2005 | Ferek-Petric | |
| 6,896,661 B2 | 5/2005 | Dekker | |
| 6,944,488 B2 | 9/2005 | Roberts | |
| 7,552,154 B2 * | 6/2009 | Moriya | 708/200 |

(Continued)

OTHER PUBLICATIONS

Cheong, et al., "A Review of the Optical Properties of Biological Tissues," from *IEEE* 1990.

(Continued)

*Primary Examiner*—George Manuel
(74) *Attorney, Agent, or Firm*—Michael C. Soldner

(57) ABSTRACT

A medical device identifies a hemodynamically unstable arrhythmia based upon optical hemodynamic sensor signals. The optical hemodynamic sensor includes a light source for transmitting light corresponding to first and second wavelengths through a blood perfused tissue of a patient and a light detector for generating optical signals corresponding to an intensity of the detected light at the first and second wavelengths. At a low motion period for the patient, optical signals are obtained from the optical hemodynamic sensor and are analyzed to determine a baseline motion level for the patient. Subsequent signals obtained from the optical hemodynamic sensor are compared to the baseline motion levels, with only those signals corresponding to periods where motion does not exceed the baseline level of motion being further analyzed to determine if they are consistent with a hemodynamically unstable arrhythmia.

20 Claims, 8 Drawing Sheets

U.S. PATENT DOCUMENTS

| | | |
|---|---|---|
| 7,596,398 B2 * | 9/2009 | Al-Ali et al. ................. 600/344 |
| 2003/0065269 A1 | 4/2003 | Vetter et al. |
| 2004/0220629 A1 | 11/2004 | Kamath et al. |
| 2004/0225332 A1 | 11/2004 | Gebhardt et al. |
| 2005/0096720 A1 | 5/2005 | Sharma et al. |
| 2007/0156190 A1 * | 7/2007 | Cinbis ........................... 607/5 |

OTHER PUBLICATIONS

Coetzee, "Noise-Resistant Pulse Oximetry Using a Synthetic Reference Signal," from *IEEE* 2000.

International Search Report, PCT/US2007/063880, Nov. 21, 2007, 7 Pages.

* cited by examiner

METHOD AND APPARATUS FOR USING AN OPTICAL HEMODYNAMIC SENSOR TO IDENTIFY AN UNSTABLE ARRHYTHMIA

BACKGROUND OF THE INVENTION

The present invention relates generally to the field of medical devices, and more particularly to a medical device capable of identifying a hemodynamically unstable arrhythmia based upon signals obtained from an optical hemodynamic sensor.

Medical devices, both internal and external, have long been used to monitor cardiac activity to detect various types of cardiac arrhythmias and to select and provide an appropriate therapy based upon the type of arrhythmia detected. Conventionally, such cardiac arrhythmia detection has been based upon an analysis of one or both of the electrical and hemodynamic functioning of the heart.

Optical hemodynamic sensors, such as pulse oximeters, have been used in medical devices to obtain data indicative of the hemodynamic function of the heart, for instance, by determining blood oxygen saturation levels. Practical applications for optical hemodynamic sensors, however, have been limited because such sensors are highly susceptible to motion; that is, movement by the patient or of the sensor tends to introduce significant noise onto an output signal of the sensor.

BRIEF SUMMARY OF THE INVENTION

The present invention is a medical device having a processor that identifies a hemodynamically unstable arrhythmia based upon signals obtained from an optical hemodynamic sensor.

The optical sensor includes a light source for transmitting a plurality of optical signals into body tissue of a patient and a light detector for receiving the plurality of signals as attenuated by transmission through the body tissue. The optical sensor further generates a plurality of corresponding output signals representative of an intensity of the attenuated signals as received.

The processor analyzes the output signals over an initial time period to assess a baseline level of motion and over a subsequent time period to assess a current level of motion. If the current level of motion does not exceed the baseline level of motion, the processor analyzes the output signals to determine if they are consistent with a hemodynamically unstable arrhythmia.

DETAILED DESCRIPTION

The present invention is directed toward a medical device, such as a cardioverter defibrillator, a pacemaker, or a cardiac monitor, that identifies a hemodynamically unstable arrhythmia based upon signals obtained from an optical hemodynamic sensor. Of interest here, in particular, are sensors capable of transmitting two or more wavelengths of light through a portion of a patient's blood perfused tissue, of receiving the transmitted signals as attenuated by transmission through the tissue, and of generating, for each transmitted wavelength, signals proportional, either directly or inversely, to an intensity of the received signals. The medical device of the present invention includes a processor for analyzing the generated signals to determine whether the signals may have been corrupted by motion. If the processor determines that motion is not a problem, the controller further analyzes the signals to determine if a state exists that is consistent with hemodynamic instability.

Figure 1:
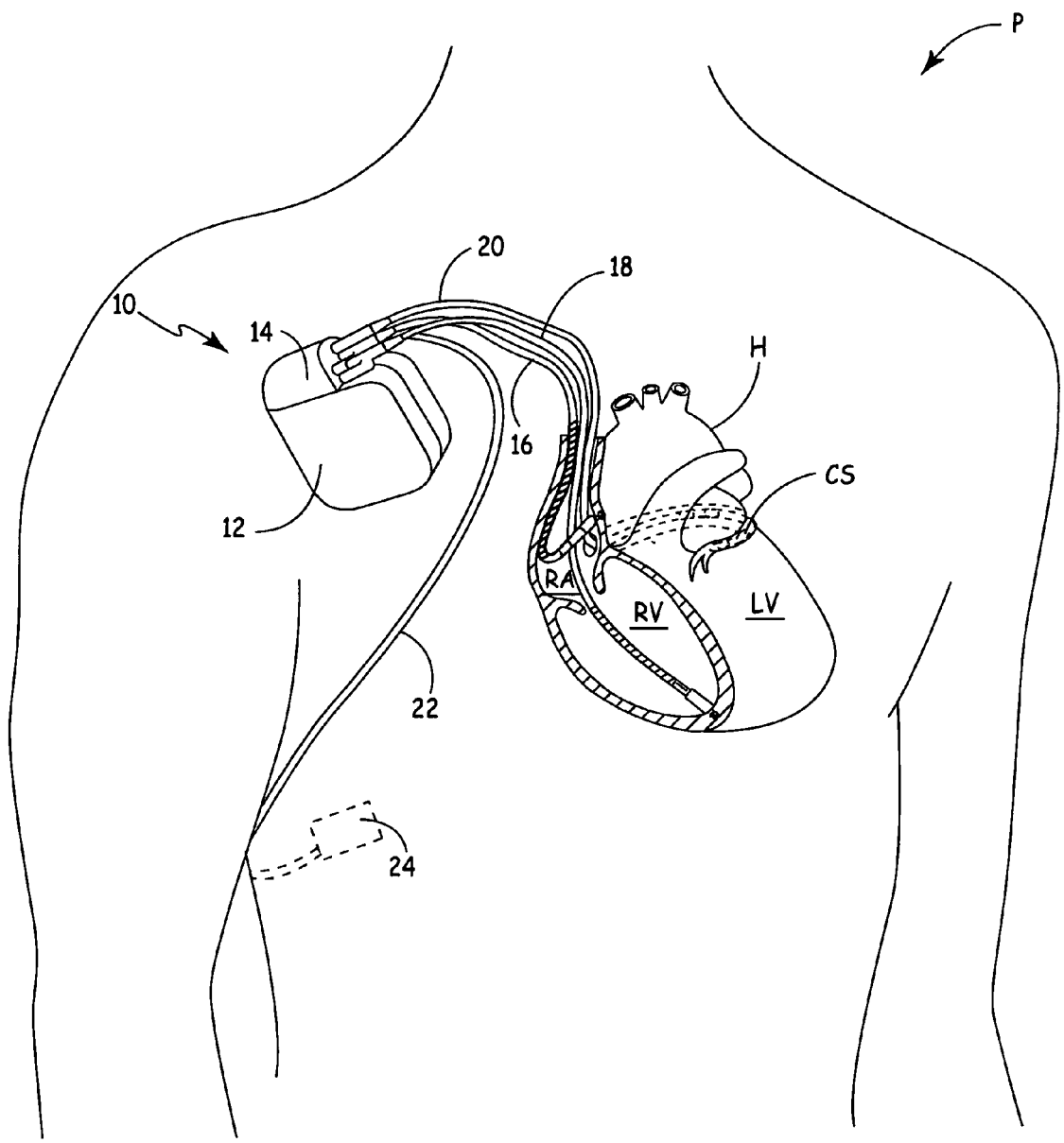
FIG. 1 is a diagram of an implantable medical device including an optical hemodynamic sensor.

FIG. 1 illustrates implantable medical device (MMD) 10 configured for both monitoring the function of and delivering therapy to heart H. In FIG. 1, heart H is shown in a partially cutaway view illustrating right atrium RA, right ventricle RV, left ventricle LV, and coronary sinus CS.

As shown in FIG. 1, IMD 10 is an implantable cardioverter defibrillator (ICD) that includes a pulse generator for delivering electrical stimulation to heart H for use in cardiac pacing therapies, cardioversion and/or defibrillation. The present invention, however, may be embodied in any medical device, implantable or external, having a multiple wavelength, optical hemodynamic sensor electrically connected thereto. Another example of an implantable medical device in which the present invention may be practiced would be a subcutaneous pacemaker or cardioverter/defibrillator implanted subcutaneously rather than transvenously.

IMD 10 includes hermetically-sealed housing 12, connector block assembly 14, right atrial (RA) lead 16, right ventricular (RV) lead 18, left ventricular (LV) lead 20, and optical hemodynamic sensor lead 22. IMD 10 further includes circuitry and a power source, which are located within housing 12, for controlling the operation of IMD 10. The circuitry communicates with leads 16, 18, 20, and 22 through electrical connectors within connector block assembly 14. A can electrode is formed on or is a part of the outer surface of housing 12, and may act as an electrode with respect to one or more of the electrodes carried by leads 16, 18 and 20.

Leads 16, 18, and 20 extend from connector block assembly 14 to right atrium RA, right ventricle RV, and coronary sinus CS adjacent left ventricle LV, respectively, of heart H. Leads 16, 18, and 20 each carry one or more sensors/electrodes for sensing electrical signals, such as electrogram (EGM) signals, attendant to the depolarization and repolarization of heart H, for providing pacing pulses for causing depolarization of cardiac tissue in the vicinity of the distal ends thereof, and for providing cardioversion shocks. When provided, a cardioversion shock is typically delivered between a combination of electrodes carried on RA and RV leads 16 and 18 and the can electrode.

Lead 22 extends from connector block assembly 14 to optical hemodynamic sensor 24, which is extravascularly-implanted—typically subcutaneously or submuscularly—at a desired location of patient P. In alternate implantable embodiments, optical hemodynamic sensor 24 may be formed on or in housing 12 of IMD 10 or may be carried by a lead from IMD 10 into a chamber of heart H or into a blood vessel. In non-implantable embodiments, a noninvasive optical hemodynamic sensor intended for use with a fleshy appendage, such as a finger or an earlobe, or the surface of the skin may be used.

Optical hemodynamic sensor 24 is preferably a multiple waveform pulse oximeter. Pulse oximeters are well known sensors commonly used with various medical devices, both implantable and external. For example, some applications of pulse oximeters are disclosed in commonly assigned U.S. Pat. Nos. 4,750,495; 5,176,137; 6,144,866; 6,198,952; or 6,944,488 to Medtronic, Inc.

Generally, pulse oximeters include a light source for emitting light through a blood perfused tissue of patient P and a light detector for generating a signal representative of an intensity of light transmitted through the blood perfused tissue to the light detector. In other embodiments, the pulse oximeter may be placed in the blood stream itself. The light passed through the tissue or bloodstream is commonly selected to be of two or more wavelengths, and most commonly, the light is selected to fall in the red part of the visible light spectrum and the infrared (IR) portion of the light spectrum. The light transmitted through the blood perfused tissue or bloodstream and received by the light detector is generally representative of hemodynamic function.

Figure 2:
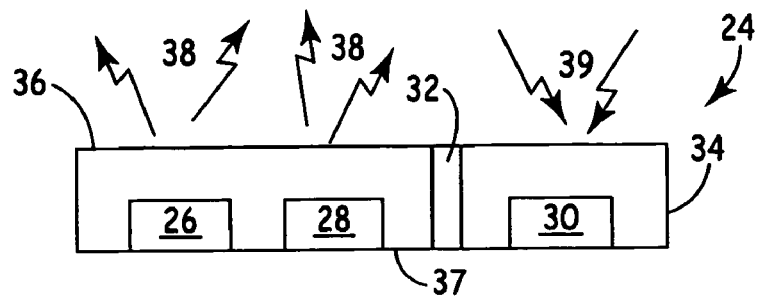
FIG. 2 is a diagram of one embodiment of the optical hemodynamic sensor.

FIG. 2 illustrates one embodiment of optical hemodynamic sensor 24, which includes red light emitting diode (LED) 26, infrared (IR) LED 28, photodiode 30, and optical barrier 32, all of which are positioned within sensor housing 34 having lens 36. In the embodiment shown in FIG. 2, LEDs 26 and 28 and photodiode 30 are each mounted on substrate 37, or a bottom surface of housing 34. As indicated by arrows 38, red and IR LEDs 26 and 28 are configured to emit light through lens 36 of housing 34, while, as indicated by arrows 39, photodiode 30 is configured to detect light received through lens 36. Optical barrier 32 is positioned to block direct transmission of light from LEDs 26 and 28 to photodiode 30.

In this embodiment, optical hemodynamic sensor preferably is subcutaneously implanted within patient P such that lens 36 is oriented toward a blood perfused tissue of patient P. In the embodiment of FIG. 2, LEDs 26 and 28 are positioned on the same side of the blood perfused tissue as photodiode 30. In alternate embodiments, LEDs 26 and 28 may be positioned on an opposite side of the blood perfused tissue as photodiode 30. This later embodiment is commonly referred to as the transmission mode and commonly used with external pulse oximeters, such as those intended for use with a fleshy appendage such as a finger or an earlobe.

Red LED 26 preferably emits light in the red portion of the visible light spectrum, while IR LED 28 preferably emits IR light in the IR portion of the light spectrum. In alternate embodiments, optical hemodynamic sensor 24 may include any two or more light sources for producing at least two different wavelengths of light. Photodiode 30 preferably receives light transmitted by LEDs 26 and 28, with an intensity of the signal received by photodiode 30 being indicative of hemodynamic function. For instance, oxygen saturation of the blood can be derived from an output of photodiode 30.

Figure 3:
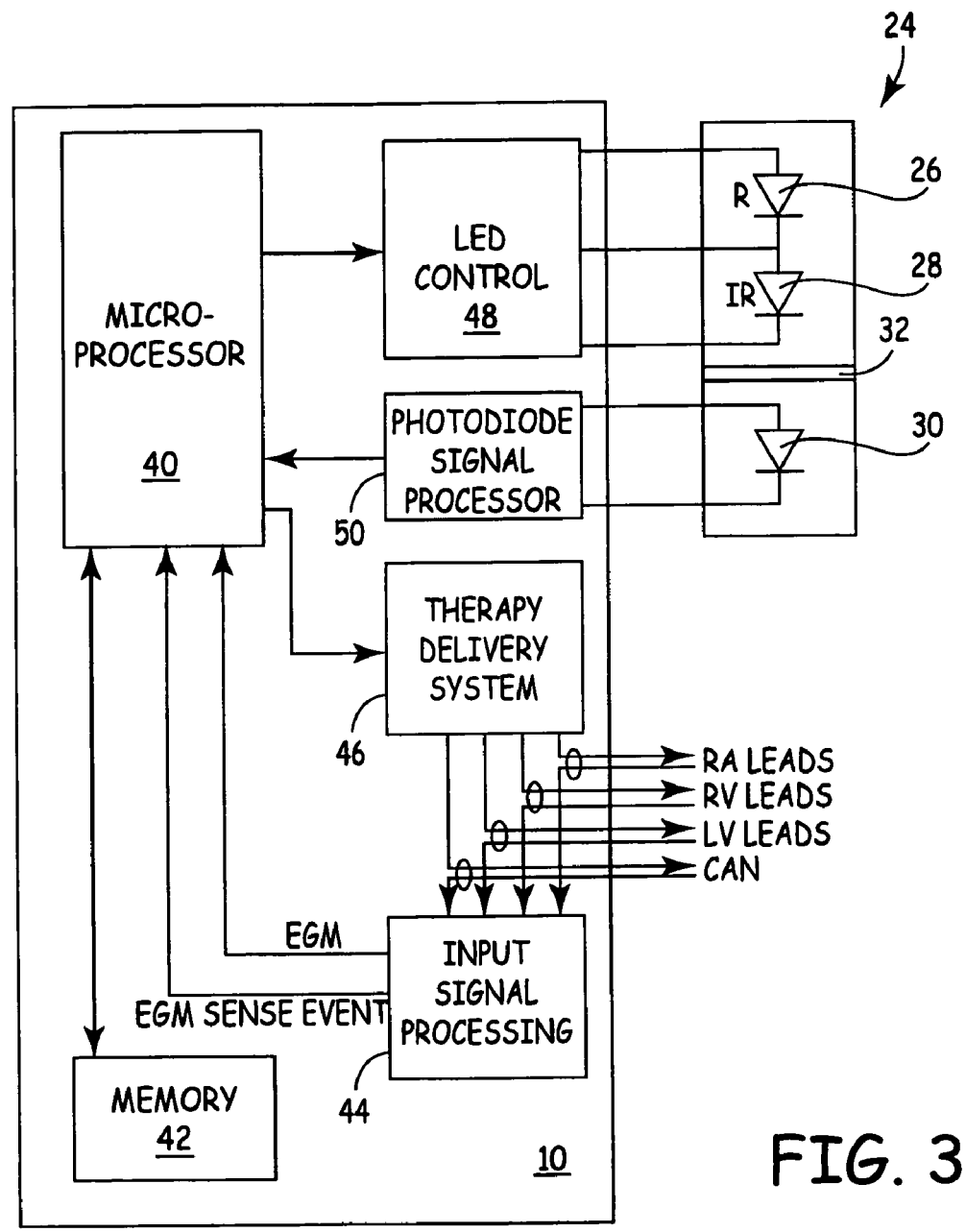
FIG. 3 is a functional block diagram of the implantable medical device and optical hemodynamic sensor.

FIG. 3 is a functional block diagram of the circuitry located within IMD 10 and within optical hemodynamic sensor 24. IMD 10 includes microprocessor circuitry 40, memory 42, input processing circuit 44, therapy delivery system 46, LED control circuitry 48, and photodiode signal processing circuitry 50. Although not shown in FIG. 3, IMD 10 further includes, among other elements, a battery for supplying power to the electronic components of IMD 10, clock circuitry for controlling timing, and telemetry circuitry to allow for communication between IMD 10 and a remote or external device, such as a programmer. Microprocessor 40 controls the functions of IMD 10 by executing firmware and program software algorithms stored in associated memory 42, such as ROM or RAM.

Input signal processing circuit 44 receives signals from RA lead 16, RV lead 18, and LV lead 20. The outputs of input signal processing circuit 44 include digitized EGM waveforms and sense event signals derived from EGM signals sensed by leads 16, 18, and 20. Input signal processing circuit 44 can be implemented with analog circuitry or with a digital signal processor.

Therapy delivery system 46 delivers cardiac pacing pulses to leads 16, 18, and and can 12 under the control of microprocessor 40. Delivery of pacing pulses is controlled in part by the selection of programmable pacing intervals, which can include atrial-atrial (A-A), atrial-ventricular (A-V), and ventricular-ventricular (VV) intervals. Therapy delivery system 46 also includes circuitry for delivering cardioversion/defibrillation therapy.

LED control circuitry 48, under the control of microprocessor 40, controls the operation of red and IR LEDs 26 and 28. Generally, red and IR LEDs 26 and 28 are sequentially operated such that only one of red and IR LEDs 26 and 28 is emitting light at a time. In one control scheme, red and IR LEDs 26 and 28 are maintained in an on state as a function of the relative amounts of red and infrared light transmitted through the blood.

When red and IR LEDs 26 and 28 are sequentially operated, the light detected by photodiode 30 will contain both information about the intensity of both the red and IR light transmitted through the blood perfused tissue. Thus, photodiode signal processor 50, under the control of microprocessor 40, demodulates the two signals and otherwise processes the signals as needed for use by microprocessor 40.

The functional block diagram illustrated in FIG. 3 is intended to be merely an example and corresponds only to a general functional organization of most presently available IMDs. Each of these functional elements may be combined into a single element or further divided into additional elements. Additionally, certain components may be relocated. For instance, LED control circuitry 48 and photodiode signal processor 50 may form a portion of optical hemodynamic sensor 24.

Figure 4:
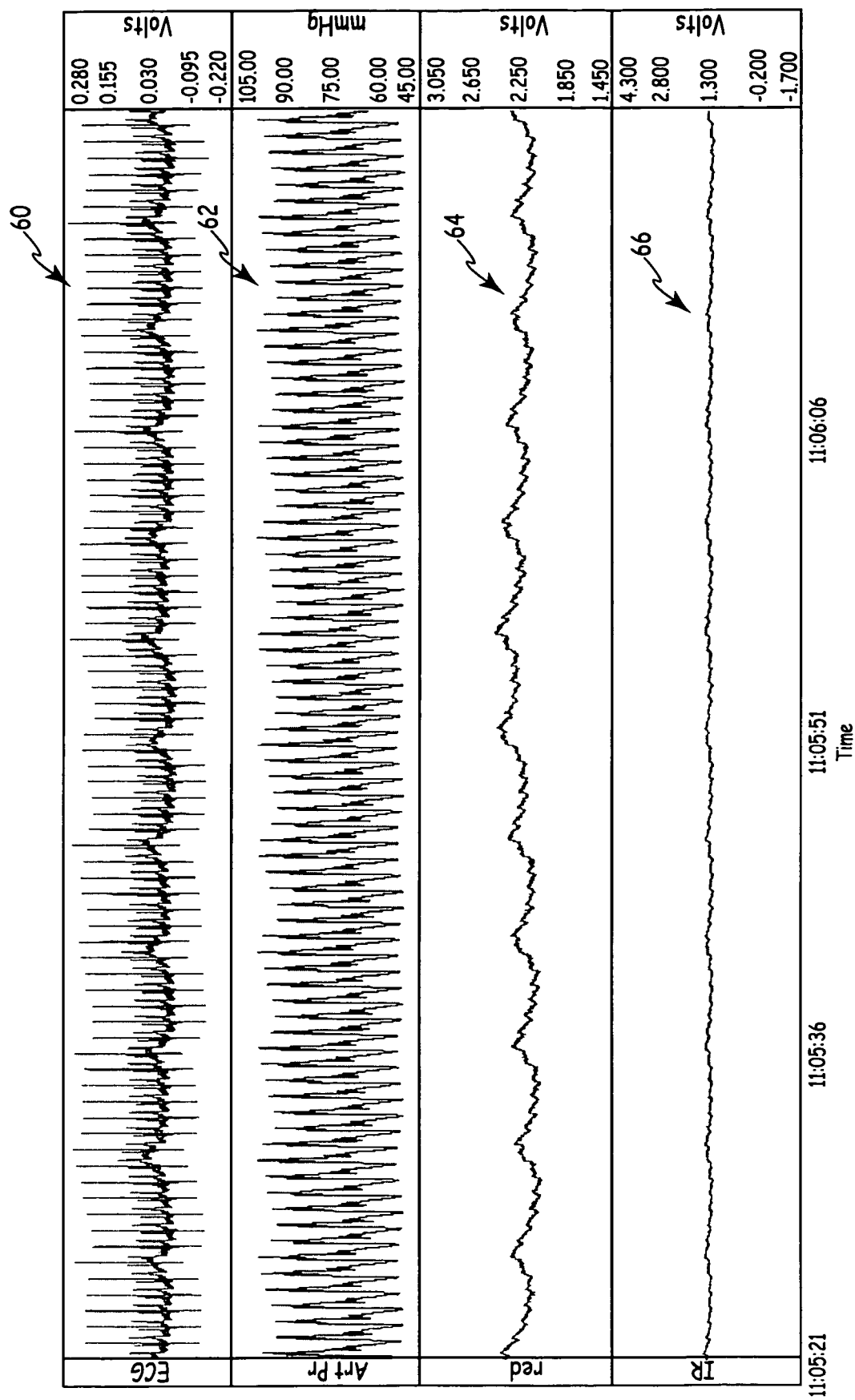
FIGS. 4-6 are graphs illustrating representative signals obtained from the optical hemodynamic sensor.
Figure 5:
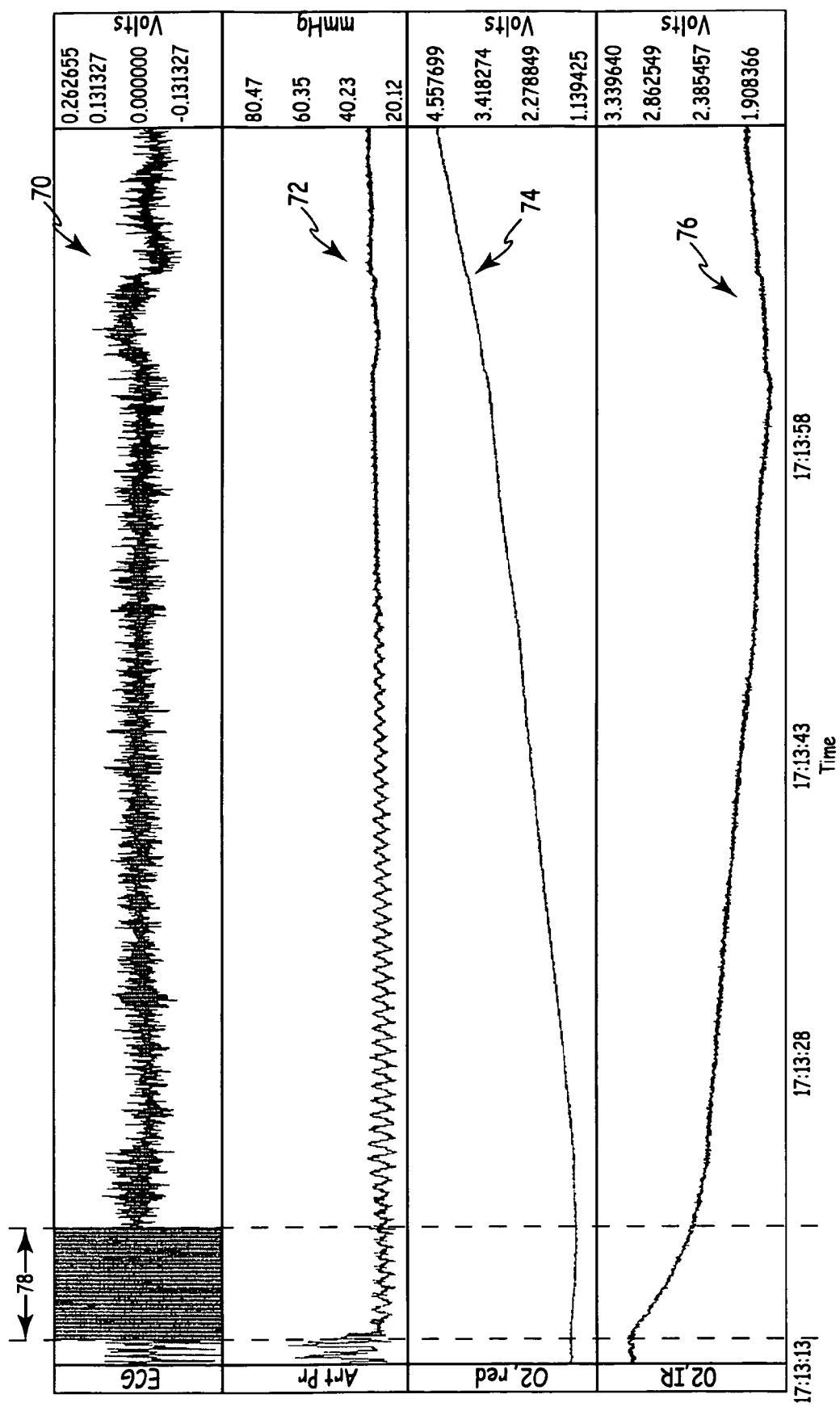
Figure 6:
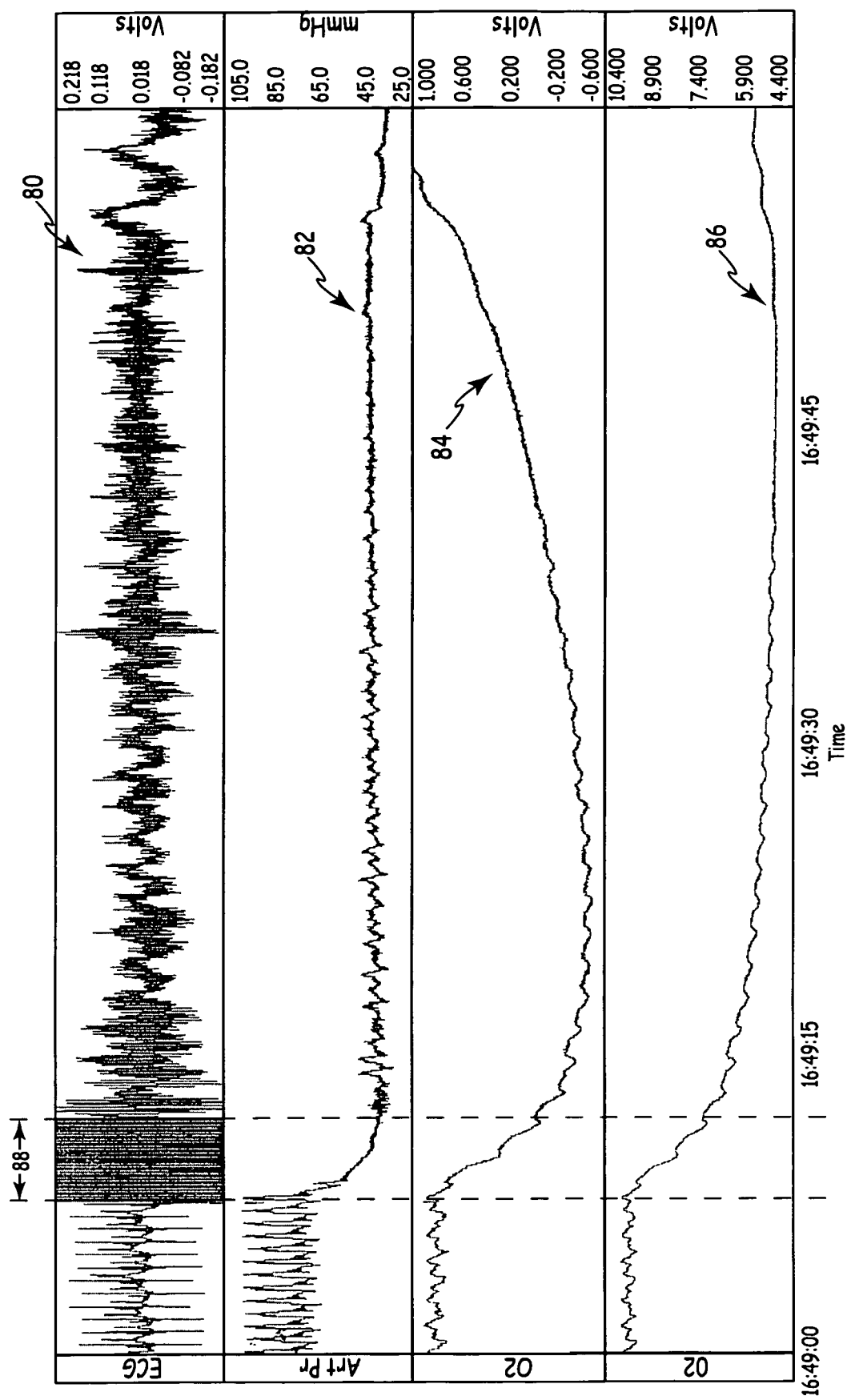

FIGS. 4-6 are graphs illustrating representative signals obtained from an optical hemodynamic sensor according to an embodiment of the present invention. Each of FIGS. 4-6 presents an ECG signal, an arterial pressure signal, a red optical signal and an infrared optical signal as a function of time. The ECG signal may be obtained from electrical sensors carried by one of the leads 16, 18, and 20. The pressure signal may be obtained from any of plurality of conventional means, including a pressure sensor located in the right ventricle RV of the heart. Red and infrared optical signals 64 and 66 are representative of red and infrared wavelength light, respectively, detected by photodiode 30. The signal outputted by photodiode 30 is inversely proportional to the intensity of the detected light.

FIG. 4 presents ECG signal 60, arterial pressure signal 62, red optical signal 64, and IR optical signal 66 for a normal sinus rhythm. FIG. 5 presents ECG signal 70, arterial pressure signal 72, red optical signal 74, and infrared optical signal 76 following an induced ventricular fibrillation initiated during time period 78 and FIG. 6 presents ECG signal 80, arterial pressure signal 82, red optical signal 84, and infrared optical signal 86 following an induced ventricular fibrillation at time period 88.

During a normal sinus rhythm, as illustrated in FIG. 4, red and infrared optical signals 64 and 66 have some variations, but tend to remain relatively constant over time. In contrast, as shown in FIG. 5, red and infrared optical signals 74 and 76 experience a significant change in value following a hemodynamically unstable ventricular fibrillation beginning during time period 78. In particular, following onset of ventricular fibrillation during time period 78, red optical signal 74 increases in value and IR optical signal 76 decreases in value.

Of course, if these signals were directly related to the intensity of the detected light, these indicator trends would be reversed. As shown in FIG. 6, red optical signal 84 experiences an initial decrease following ventricular fibrillation, but then shortly begins increasing in value, while infrared optical signal 86 decreases in value.

For optical signals inversely related to incident intensity, a hemodynamically unstable arrhythmia is uniquely marked by an increase in a red optical signal and a decrease in an IR optical signal. Thus, this characteristic may be used by IMD 10 to identify the occurrence of hemodynamically unstable arrhythmias for which cardioversion/defibrillation may be required. However, the optical signals can be degraded by motion of the patient, which introduces noise and affects the optical signals. The optical signals generally comprise a relatively small AC portion residing on a relatively large DC portion. The DC portion of the optical signal contains valuable hemodynamic information. The noise introduced by motion is generally characterized by a high frequency and a peak-to-peak variation that tends to overwhelm the AC portion of the optical signal and alters the DC portion.

Figure 7:
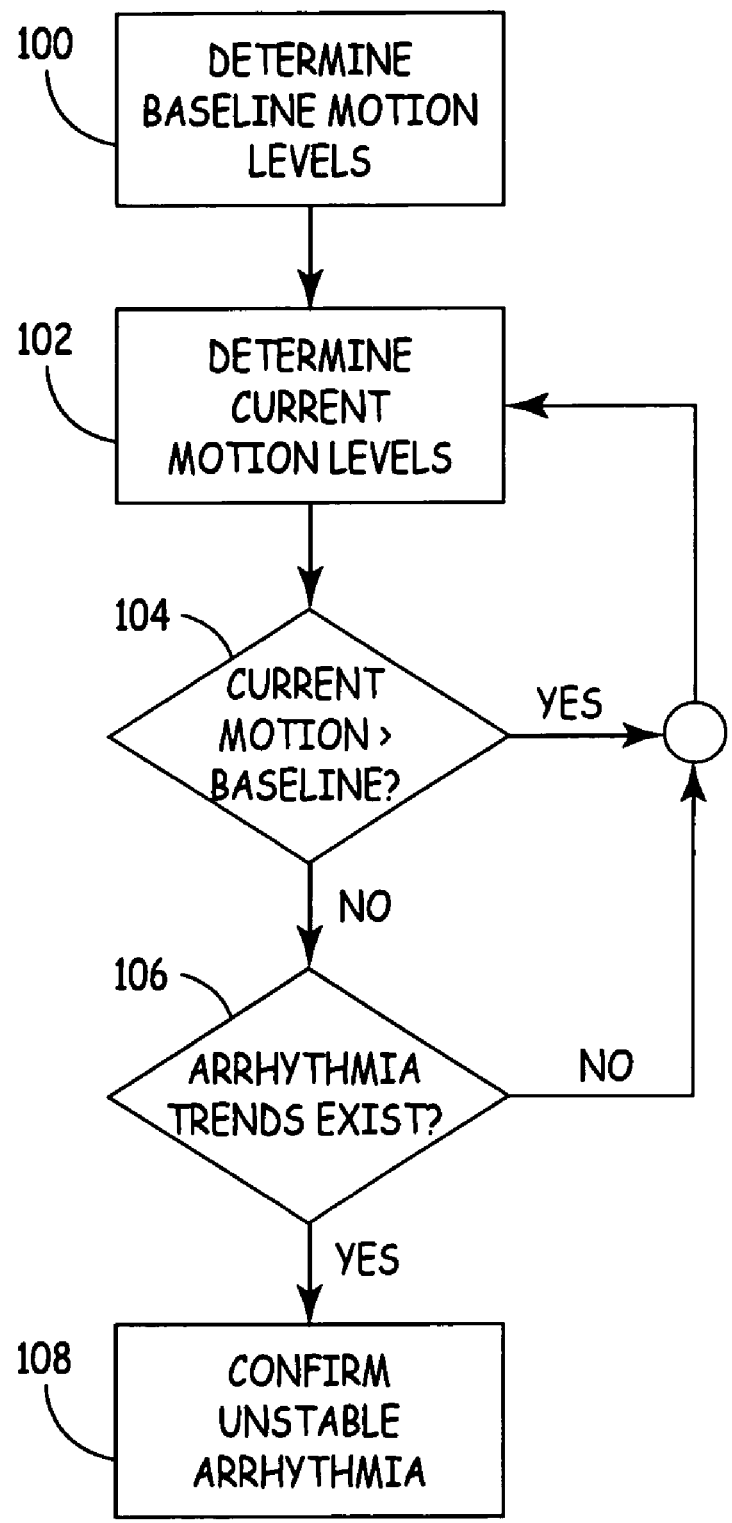
FIGS. 7-9 are flow charts illustrating an algorithm for use in the implantable medical device for detecting a hemodynamically unstable arrhythmia.

FIG. 7 is a flow chart illustrating an algorithm for use with IMD 10 for detecting a hemodynamically unstable arrhythmia. At step 100, a baseline motion level is determined at a time of relatively low patient movement. This baseline motion level can be determined at a prescribed time, such as in the middle of the night when the patient is likely asleep. Alternately, a motion sensor, such as an accelerometer, can be used to ascertain periods of relatively low patient movement. The baseline motion level is determined by analyzing the red and IR optical signals obtained from optical hemodynamic sensor 24. Step 100 is preferably performed on a periodic basis, such as on a daily or weekly basis. Alternately, the baseline motion level may be determined at non-periodic times which are triggered by the occurrence of an event, such as by the interrogation by an external programmer communicatively connected to IMD 10.

At step 102, the current motion level is determined. As with the baseline motion level, the current motion level is determined by analyzing the red and IR optical signals. At step 104, the current motion level is compared to the baseline motion level. If the current motion level exceeds the baseline motion level, it is assumed that the optical signals are too unreliable to be used as a basis for detecting a hemodynamically unstable arrhythmia and the algorithm returns to step 102 to reassess a current motion level. If the current motion level exceeds the baseline motion level, it is assumed by the method of the present invention that any meaningful hemodynamic information contained in the optical signals has been corrupted by motion artifacts. Further, the presence of motion is an indicator that the patient is hemodynamically stable; that is, a hemodynamically unstable arrhythmia is unlikely to be accompanied by significant motion by the patient.

If the current motion level does not exceed the baseline motion level, at step 106 the red and IR optical signals are evaluated to determine if the optical signals are consistent with a hemodynamically unstable arrhythmia. As described above, a hemodynamically unstable arrhythmia is marked by an increase in the red signal (i.e., a decrease in intensity of the detected red light) and a decrease in the IR signal (i.e., an increase in the intensity of the detected infrared light). If the signals are inconsistent with a hemodynamically unstable arrhythmia, the algorithm returns to step 102 to reassess a current motion level.

In some embodiments of the present invention, if the signals are consistent with a hemodynamically unstable arrhythmia, at step 108, the algorithm notes the occurrence of the arrhythmia so that IM 10 may provide therapy to treat the arrhythmia. In other embodiments, the algorithm of FIG. 7 is only used to confirm an arrhythmia detection made using conventional methods based on the electrical function of the patient (i.e., the EGM signal). In this embodiment, a baseline motion level may be determined on a periodic basis, but steps 102-108 are only executed when IMD 10 detects an arrhythmia via conventional means.

Figure 8:
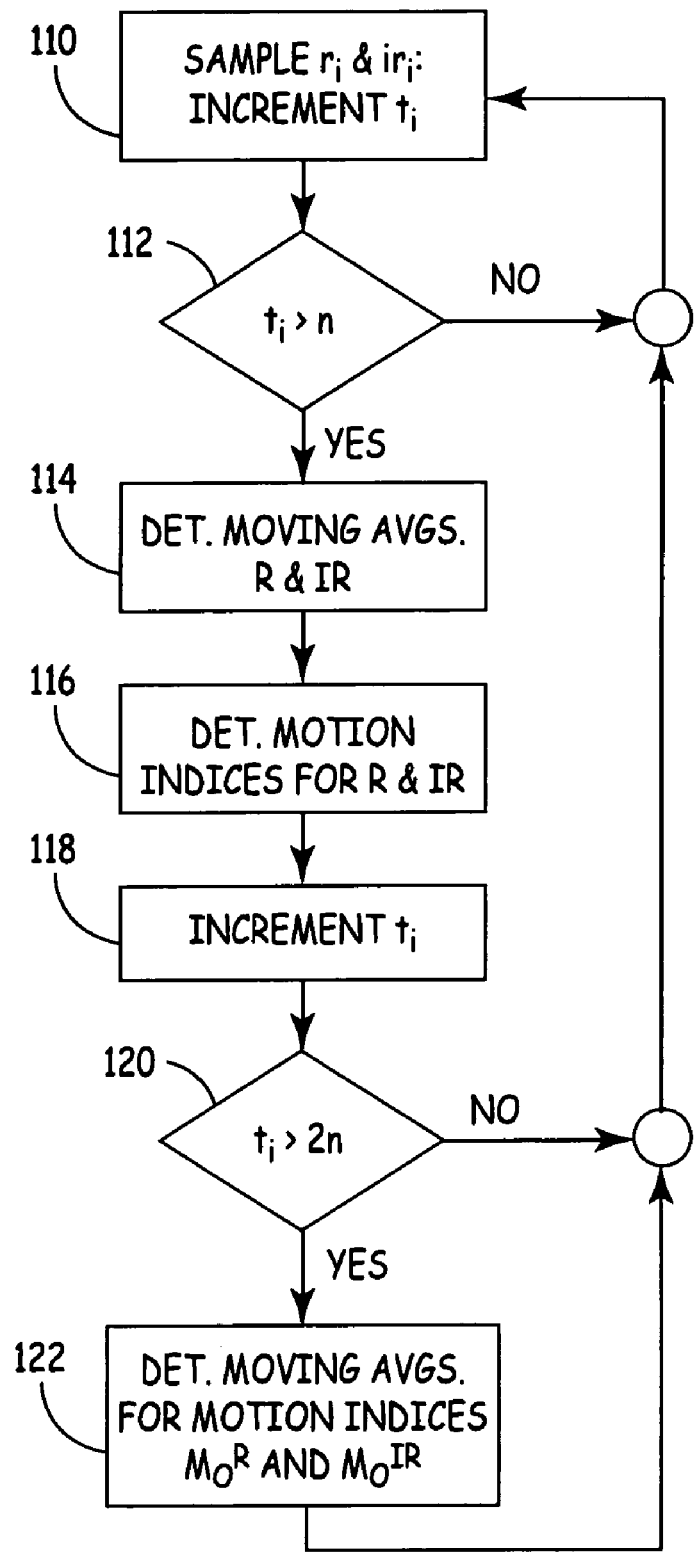

FIG. 8 is a flowchart illustrating one method for determining a baseline motion level. The method of FIG. 8 assumes the presence of an analog-to-digital converter for sampling the red and infrared optical signals and a running register of size n for storage of n digital samples each of the red and the infrared optical signals.

At step 110, the red optical signal and the IR optical signal are each digitally sampled at time instant $t_i$ and respective digital samples $r_i$ and $ir_i$ are stored in the running buffer. After the optical signals are sampled, time instant $t_i$ is incremented. Initially, time instant $t_i$ is set $t_0$. Step 112 serves to ensure that step 110 is performed n times prior to the method advancing to the next step.

Once the running buffer is filled with n samples $r_i$ and $ir_i$ of the red and IR optical signals, the method progresses to step 114 where simple moving averages R and IR of optical signals samples $r_k$ and $ir_k$, respectively, are determined from the n samples $r_i$ and $ir_i$ of the optical signals. These simple moving averages help smooth the sampled data and make it easier to spot trends therein. At step 116, motion indexes are computed for the moving averages R and IR determined at step 114. In one embodiment, the motion index of the red optical signal is the absolute value of the difference between the sample $r_i$ and the moving average R at a time instant $t_i$. In other embodiments, the motion index may be computed as a standard deviation over the n sample period. At step 118, time instant $t_i$ is incremented. Step 120 ensures that steps 110 and 118 are performed n+m times prior to advancing to the next step, where m is an integer variable.

At step 122, a baseline motion level for each of the red and the IR optical signals is determined as simple moving averages $M_0^R$ and $M_0^{IR}$ of m values of the corresponding motion indices. The motion index determined at step 116 serves to provide information about how widely the samples are deviating. At a relatively low motion level, there will be some variation in the samples, but this variation should be relatively low. When motion is present, this variation will be substantially larger. As will be shown in FIG. 9 below, the current motion level of a patient may be determined via a method similar to the method of FIG. 8 for determining a baseline level of motion.

Figure 9:
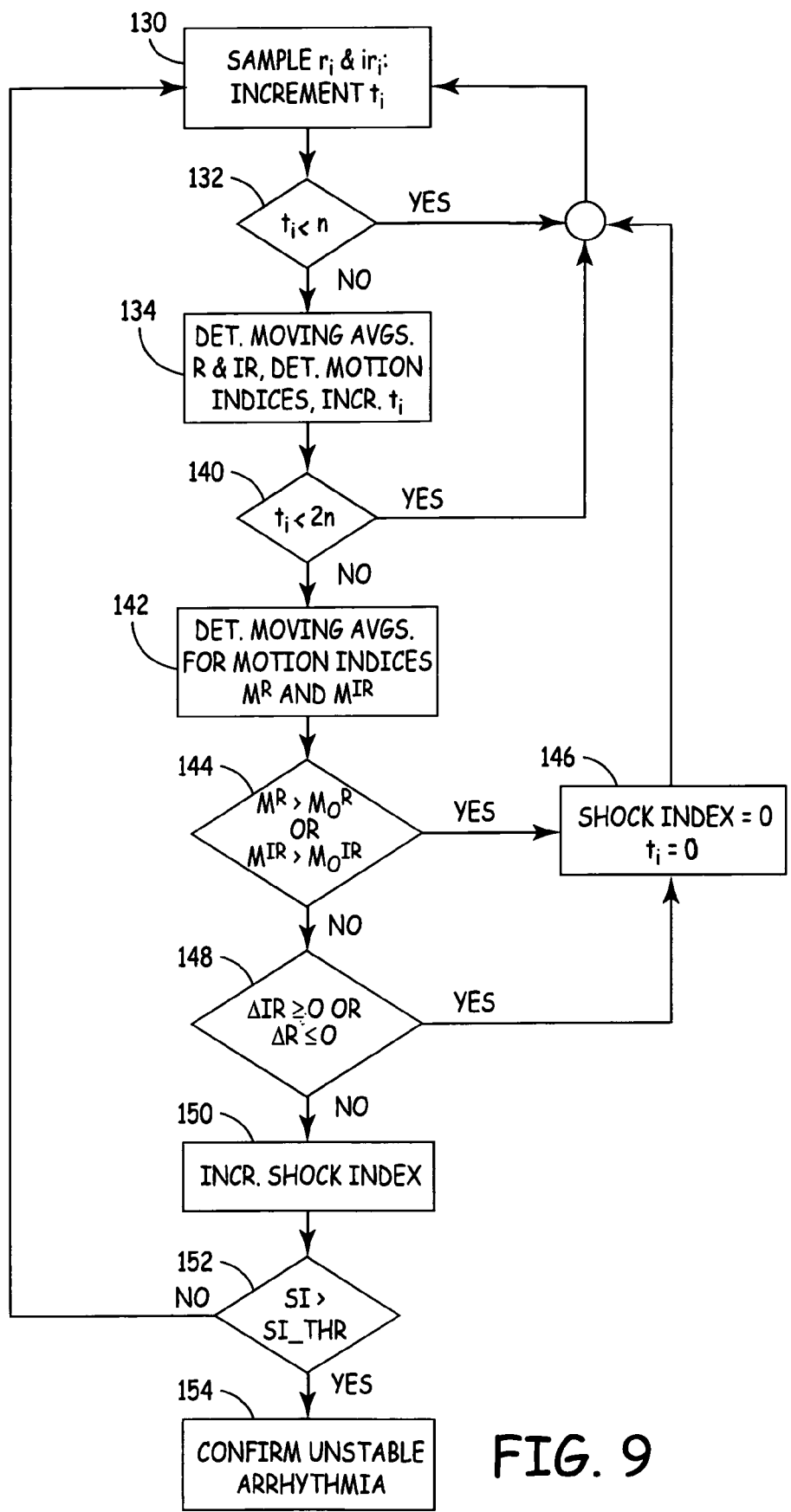

FIG. 9 is a flowchart illustrating one method for determining a current motion level and analyzing optical signals obtained from an optical hemodynamic sensor to detect the presence of a hemodynamically unstable arrhythmia. The method illustrated in FIG. 9 may be a stand-alone process. Alternately, it may be called to verify an arrhythmia detection made by another process; for instance, a conventional EGM analysis. Steps 130-142 illustrated in FIG. 9 are similar to steps 110-122 identified in FIG. 8. At the initiation of this method, a shock index SI is set at zero and a sampling time instant $t_i$ is set $t_0$. In accordance with this method, upon identifying some indicators of a hemodynamically unstable arrhythmia, the shock index SI is increased. As will be described below, only when the shock index SI reaches a shock index threshold SI_thr does the method report (or confirm) the presence of an unstable arrhythmia.

At step 130, the red optical signal and the infra-red optical signal are each digitally sampled at time instant $t_i$ and respective digital samples $r_i$ and $ir_i$ are stored in the running buffer. After the optical signals are sampled, time instant $t_i$ is incremented. Step 132 serves to ensure that step 130 is performed n times prior to the method advancing to the next step.

Once the running buffer is filled with n samples $r_i$ and $ir_i$ of the red and infra-red optical signals, the method progresses to step 134 where simple moving averages R and IR of optical signal samples $r_i$ and $ir_i$, respectively, are determined from the n samples $r_i$ and $ir_i$ of the optical signals; motion indices are computed for moving averages R and IR as the absolute value of the difference between the sample $r_i$ (or $ir_i$) and the moving average R (or IR) at a time instant $t_i$; and time instant $t_i$ is incremented. Alternatively the motion indices can also be calculated as the respective standard deviations of the red and the infra-red samples. Step 140 ensures that steps 130-134 are performed n+m times prior to advancing to the next step.

At step 142, a current motion level for each of the red and the infra-red optical signals is determined as simple moving averages $M^R$ and $M^{IR}$ of m values of the corresponding motion indices. This average motion index serves to provide information about how widely the samples are deviating. At a relatively low motion level, there will be some variation in the samples, but this variation should be relatively small. When motion is present, this variation will be substantially larger.

In an alternate embodiment, Steps 134, 140 and 142 may be accomplished by collecting n+m samples first, followed by a low-pass filtering, where the filtering frequency corresponds to the duration of the n samples. Deviation of the samples from the low-passed version of the signals may be used to compute the motion index. The motion index may be computed as the mean of absolute deviations, the mean square of deviations, a standard deviation or a correlation coefficient. An example of using the correlation coefficient as a motion index may be when a least square linear fit is used as the means of filtering.

At step 144, the current motion level $M^R$ and $M^{IR}$ are compared to baseline motion levels $M_0^R$ and $M_0^{IR}$. If the current motion level exceeds a multiple $\alpha$ of the baseline motion, the method progresses to step 146 where both the shock index SI and the time instant $t_i$ are reset $t_0$ or zero. These values are reset, or reinitialized, because the presence of motion calls into question any previously determined indicators of a hemodynamically unstable arrhythmia.

At step 148, the moving averages R and IR of the samples of the red and infra-red optical signals are analyzed to determine if they are consistent with a hemodynamically unstable arrhythmia. As described above, an unstable arrhythmia is characterized by a decrease in the intensity of the detected red light and an increase in the intensity of the detected infra-red light. Using optical hemodynamic sensor 24 illustrated above, the red and infra-red optical signals are inversely related to intensity. Thus, at step 148, either a negative slope of the red moving average R or a positive slope of the infra-red moving average IR indicates that the patient is not experiencing a hemodynamically unstable arrhythmia and the method progresses to step 146 to reset the shock index SI and the time instant $t_i$.

Conversely, a hemodynamically unstable arrhythmia is indicated if the red moving average R has a positive slope and the infra-red moving average IR has a negative slope. Thus, at step 150, the shock index SI is incremented. At step 152, the shock index SI is compared to the shock index threshold SI_thr to determine whether consistent indicators of a hemodynamically unstable arrhythmia have been detected. Only when the shock index SI exceeds the shock index threshold SI_thr does the method illustrated in FIG. 9 confirm that a hemodynamically unstable arrhythmia exists. Alternate embodiments may include additional tests for identifying a hemodynamically unstable arrhythmia. For instance, the method may require that the slopes of either or both the red and infrared optical signals exceed threshold slopes.

The methods presented in FIGS. 8 and 9 are only presented as examples of ways in which the present invention may be implemented and is not intended to be limiting, and those skilled in the art will recognize numerous possible variations. The present invention is a medical device that identifies a hemodynamically unstable arrhythmia based upon signals obtained from an optical hemodynamic sensor. In accordance with the present invention, the medical device obtains signals from the optical hemodynamic sensor for a time period corresponding to a low motion period for the patient. These optical signals are analyzed to determine a baseline motion level for the patient. Subsequent signals obtained from the optical hemodynamic sensor are compared to the baseline motion levels, with only those signals corresponding to periods where motion does not exceed the baseline level of motion being further analyzed to determine if they are consistent with a hemodynamically unstable arrhythmia.

Although the present invention has been described with reference to preferred embodiments, workers skilled in the art will recognize that changes may be made in form and detail without departing from the spirit and scope of the invention.

The invention claimed is:

1. A medical device comprising:
    an optical sensor for transmitting into body tissue of a patient a plurality of optical signals, receiving the plurality of signals as attenuated by transmission through the body tissue, and generating a plurality of corresponding output signals representative of an intensity of the attenuated signals as received; and
    a processor for analyzing the output signals over an initial time period to assess a baseline level of motion and analyzing the output signals over a subsequent time period to determine whether a current level of motion exceeds the baseline level of motion;
    wherein the processor further analyzes the output signals over the subsequent time period to determine whether the patient is experiencing a hemodynamically unstable arrhythmia.

2. The medical device of claim 1 and further comprising a therapy delivery system for delivering at least one of a cardiac pacing, a cardioversion, or a defibrillation therapy to the patient, wherein the therapy delivery system delivers at least one of the cardiac pacing, the cardioversion, or the defibrillation therapies to the patient if the processor determines that the patient is experiencing a hemodynamically unstable arrhythmia.

3. The medical device of claim 1 and further comprising a sensor for detecting an electrical signal attendant to the depolarization and repolarization of the patient's heart, wherein the processor initially analyzes the electrical signal to determine if the patient is experiencing an arrhythmia and, if it is determined that the patient is experiencing an arrhythmia, further analyzes the output signals to determine whether the patient is experiencing a hemodynamically unstable arrhythmia.

4. The medical device of claim 1, wherein the processor determines a motion level for a time period by calculating a plurality of first moving averages for each of the output signals over a relevant time period, a plurality of motion indices indicative of variations of each output signal and the corresponding first moving average, and a plurality of second moving averages for each of the motion indices over the relevant time period.

5. The medical device of claim 1, wherein the optical sensor comprises a first light emitter capable of transmitting a first optical signal characterized by a first wavelength and a second light emitter capable of transmitting a second optical signal characterized by a second wavelength different from the first wavelength.

6. The medical device of claim 5, wherein the first wavelength is in a range of about 550 nanometers to about 750 nanometers and the second wavelength is in a range of about 750 nanometers to about 2.5 micrometers.

7. The medical device of claim 6, wherein the sensor signals comprise a first and a second sensor signal corresponding to an intensity of a respective one the first and the second optical signal as received by the optical hemodynamic sensor, and wherein the processor determines whether the patient is experiencing a hemodynamically unstable arrhythmia by determining if an intensity of the first sensor signal is decreasing and an intensity of the second sensor signal is increasing.

8. The medical device of claim 1, wherein the medical device is an implantable medical device.

9. The medical device of claim 1 wherein the processor further analyzes the output signals over the subsequent time period to determine whether the patient is experiencing a hemodynamically unstable arrhythmia if the current level of motion does not exceed the baseline level of motion.

10. A medical device comprising:
an optical hemodynamic sensor for producing sensor signals indicative of hemodynamic function of a patient;
a processor for determining from the sensor signals whether the sensor signals are corrupt sensor signals due to patient motion or uncorrupt sensor signals, and for determining whether the patient is experiencing a hemodynamically unstable arrhythmia based upon the uncorrupt sensor signals.

11. The medical device of claim 10 and further comprising a therapy delivery system for delivering at least one of a cardiac pacing, a cardioversion, or a defibrillation therapy to the patient, wherein the therapy delivery system delivers at least one of the cardiac pacing, the cardioversion, or the defibrillation therapies to the patient if the processor determines that the patient is experiencing a hemodynamically unstable arrhythmia.

12. The medical device of claim 10, wherein the optical hemodynamic sensor comprises a light source for emitting light signals corresponding to at least two wavelengths.

13. The medical device of claim 10, wherein the sensor signals correspond to an intensity of light signals corresponding to at least two wavelengths as attenuated by transmission through body tissue, and wherein the processor determines if the patient is experiencing a hemodynamically unstable arrhythmia based upon a slope of each sensor signal.

14. A method for detecting an unstable arrhythmia in a patient, the method comprising:
obtaining sensor signals from an optical hemodynamic sensor, wherein the sensor signals are indicative of a hemodynamic function of the patient;
determining from an initial period of the sensor signals a baseline motion level of the patient;
determining from a subsequent period of the sensor signals a current motion level of the patient; and
analyzing the sensor signals if the current motion level does not exceed the baseline motion level to determine whether the patient is experiencing a hemodynamically unstable arrhythmia.

15. The method of claim 14 and further comprising:
delivering at least one of a cardiac pacing, a cardioversion, or a defibrillation therapy to the patient if it is determined that the patient is experiencing a hemodynamically unstable arrhythmia.

16. The method of claim 14, wherein obtaining sensor signals from the optical hemodynamic sensor comprises:
transmitting into body tissue of the patient a first optical signal characterized by a first wavelength and a second optical signal characterized by a second wavelength different than the first wavelength;
receiving the first and second signals as attenuated by transmission through the body tissue; and
generating a first and a second sensor signal, each of the first and second sensor signals being representative of an intensity of the attenuated signals as received.

17. The method of claim 16, wherein the first wavelength corresponds to red visible light spectrum and the second wavelength corresponds to infrared light.

18. The method of claim 17, wherein analyzing the sensor signals to determine whether the patient is experiencing a hemodynamically unstable arrhythmia comprises:
determining whether an intensity of the first attenuated signal is decreasing; and
determining whether an intensity of the second attenuated signal is increasing.

19. The method of claim 14, wherein determining from the initial period of the sensor signals the baseline motion level of the patient comprises:
determining a plurality of first moving averages for each of the sensor signals over the initial time period;
determining a plurality of motion indices indicative of variations of each sensor signal and the corresponding first moving average; and
determining a plurality of second moving averages for each of the motion indices over the initial time period.

20. The method of claim 14, wherein determining from the subsequent period of the sensor signals the baseline motion level of the patient comprises:
determining a plurality of first moving averages for each of the sensor signals over the subsequent time period;
determining a plurality of motion indices indicative of variations of each sensor signal and its corresponding first moving average; and
determining a plurality of second moving averages for each of the motion indices over the subsequent time period.

* * * * *